United States Patent [19]

Bolton et al.

[11] Patent Number: 4,668,228

[45] Date of Patent: May 26, 1987

[54] DEBRIDING TAPE

[75] Inventors: Laura L. Bolton, Metuchen; Barry E. Constantine, Island Heights, both of N.J.

[73] Assignee: Johnson & Johnson Products, Inc., New Brunswick, N.J.

[21] Appl. No.: 710,817

[22] Filed: Mar. 12, 1985

[51] Int. Cl.$^4$ ............................................. A61F 13/02
[52] U.S. Cl. .................................. 604/307; 128/155; 424/94.62; 604/289; 604/304
[58] Field of Search ............... 128/155, 156; 604/289, 604/290, 291, 292, 293, 294, 303, 304, 307, 308; 424/26, 27, 28, 94, 78

[56] References Cited

U.S. PATENT DOCUMENTS

| | | | |
|---|---|---|---|
| 3,983,209 | 9/1976 | Schmitt | 424/78 |
| 4,307,081 | 12/1981 | Klein et al. | 424/94 |
| 4,310,509 | 1/1982 | Berglund et al. | 128/155 |
| 4,413,621 | 11/1983 | McCracken et al. | 128/156 |

OTHER PUBLICATIONS

The Merck Index, Martha Windholz, ed., 1983, p. 322.

*Primary Examiner*—C. Fred Rosenbaum
*Assistant Examiner*—Denise Whelton

[57] ABSTRACT

Debriding tapes are disclosed which contain a proteolytic enzyme useful for debridement of eschar and necrotic tissue, e.g., subtilisin, bromelain, in dry powdered form on the adhesive mass surface of an occlusive or semi-occlusive surgical adhesive tape.

9 Claims, No Drawings

DEBRIDING TAPE

BACKGROUND OF THE INVENTION

This invention relates to a delivery system for any enzyme useful for the debridement of necrotic tissue from body lesions such as burns, traumatic wounds and cutaneous ulcers, e.g., a debriding enzyme and more particularly to a surgical adhesive tape containing a debriding enzyme, i.e., a debriding tape.

Debridement of necrotic tissue from burns, traumatic wounds and cutaneous ulcers is essential before repair can progress normally. There are existing products on the market for this purpose but they do not work as quickly, safely and painlessly as is desirable, and many are relatively ineffective. Existing commercial debriding products are all creams, sprays, lotions or ointments. These dilute the enzymatic debriding agents so that their delivery is impeded. Only a fraction of the total applied debriding agent reaches the necrotic tissue at any one time. Therefore, a large total amount of enzyme must be contained in the formulation to produce a debriding effect, but these are painful to apply and contain so much enzyme that the local healthy tissue may be attacked. Furthermore, many cream or ointment-type debriding products cannot be sterilized without inactivating the enzyme and, therefore, are not sold as sterile products. These debriding ointments are not stable at room temperatures and must be stored under refrigeration. The debriding tape of the present invention overcomes the serious defects of these existing products, and is different in construction and operation from all prior art debridement methods and materials, and is easily distinguished therefrom.

SUMMARY OF THE INVENTION

The present invention is a debriding tape, made from an occlusive or semi-occlusive, non-gel, non-bioerodible, surgical adhesive tape which contains on the adhesive mass surface of said surgical adhesive tape a debriding enzyme (either a proteolytic or a non-proteolytic enzyme useful for debridement of eschar and necrotic tissue) in dry, powdered form.

When the debriding tape is applied to a burned surface, water from the wound which cannot penetrate the occlusive tape backing collects and activates the debriding enzyme. Normally, wounds can be debrided in less than 24 hours. If the burn site is moistened with a small amount of sterile water before the tape is applied, the wounds can be debrided in 2-4 hours.

Burn patients who are not treated for 48 hours after a severe burn may be too dehydrated to transpire adequate water for activating the enzyme. In these cases, sterile water may be applied to the burn surface before application of the debriding tape. Most fresh burns could be successfully treated with the debriding tapes of the present invention in less than 24 hours without the application of excess water to the burn surface.

Prior Art Distinguished

Schmitt U.S. Pat. No. 3,983,209, entitled "Method for Treating Burns" teaches treating burns in animals by applying to the burned surface a proteolytic enzyme known to be useful for debridement of eschar and necrotic tissue to permit healing, e.g., papain, trypsin, lysozyme, streptokinase, fibrinolysin, Pinguinain, Travase and Bromelain, in a specified hydrophobic, bioerodible polymer, which polymer on bioerosion on the burned surface over a prolonged period of time slowly releases the proteolytic enzyme in a sustained release manner.

The debriding tape of the present invention does not act in a sustained release manner but rather in an immediate, non-sustained release manner. Most or all of the enzyme which is in dry, powdered form on the outer surface of the adhesive mass, actually is applied to the burned surface at once, so that as moisture from the wound activates the enzyme, all of the enzyme begins debriding the eschar and necrotic surfaces which process is normally fully complete in less than 24 hours so that the eschar has been softened enough to be wiped away easily.

King U.S. Pat. No. 3,413,006, entitled "Novel Dressing and Use Thereof" teaches treating burns with a dressing made of or containing a hydrophilic, polymer gel, e.g., crosslinked poly(ethylene oxide) which can contain various chemotherapeutic agents, including various enzymes. That patent does not teach a tape construction like that of the present invention, nor any concept of debriding a burn. We have found that gel dressings do not work as well as the debriding tape described herein for our rapid debriding purposes, and we exclude such type of tapes from the present inventive concept.

Lenz et al. U.S. Pat. No. 4,320,753 discloses a bandage prepared from a polymer prepared from beta-malolactone or its derivatives, to which is bonded an enzyme used in burn debridement. That patent addresses the incorporation of debriding enzymes into biodegradable films. As the film degrades, enzyme is released to interact with the necrotic tissue to be digested. This process is slow because it depends on degradation of the film by biological processes. In contrast, in the present invention, the enzyme is all immediately available to the tissue, ready to act as soon as it is activated by moisture which emanates from the wound.

Debriding Enzymes

The debriding enzymes useful in the present invention are well known materials which were used in a different manner. U.S. Pat. No. 3,983,209 taught that proteolytic enzymes useful for debridement of eschar and necrotic tissue to permit wound healing include papain, trypsin, collagenase, subtilisins A and B, ficin, pepsin, lysozyme, streptokinase, fibrinolysin, Pinguinain, and bromelain or their active fractions. Other known debriding enzymes include papain, the "escharase" fraction of bromelain, pepsin, chymotrypsin, pancreatic lipase, n-acetylcysteine. Particular enzyme products derived from bromelein are taught in U.S. Pat. Nos. 4,197,291, 4,307,081 and 4,361,551. For reasons of availability, ease of obtaining regulatory approval, and economy, we prefer to use subtilisin A or B as our most preferred debriding enzyme, with other preferred debriding enzymes being active fractions of bromelain or other pharmaceutically acceptable enzymes.

The debriding enzymes which are useful in the debriding tapes of the present invention are solids capable of being ground into powder form. This allows them to be easily distributed relatively evenly on the active part of the debriding tape.

The debriding enzyme is most desirably applied to the surface of the adhesive mass to be placed nearest the necrotic tissue because it has been found most efficacious to apply the full quantity of enzyme directly to the eschar which is to be debrided. If enzyme is incorporated in the adhesive mass, this will also work but not as well; or at least the portion of the enzyme which is incorporated within the adhesive mass would take longer to have any effect on the eschar because of its slower delivery. Thus, the most desired version of the debriding tape of the present invention would have substantially all of the debriding enzyme applied to the outer surface where it is immediately available.

The quantities of enzyme on the debriding tape are not critical, but it is desired that a relatively large amount be applied to the critical areas at once. We have found that amounts on the order of from 0.5 mg of subtilisin A or (885 PCU[1]) to 5 mg or 8850 PCU/cm$^2$ of burn area can be used, depending on the depths of necrotic tissue to be removed. What is desired is to use an effective debriding amount of the particular enzyme used.

[1]PCU is an abbreviation of Proteolytic Casein Units as defined in the Food Chemicals Codex, 3rd Edition, pages 495-496. One PCU is the quantity of enzyme that produces the equivalent of 1.5 μg/ml of L-tyrosine per minute of incubation with a standard casein solution at 37° C., pH 7.0.

The effective amount could differ depending upon the desired application. For example, for burns the amount would be generally on the order of 885 PCU/cm$^2$ while for deeper ischemic ulcers, the amount would be generally on the order of 2000-3000 PCU/cm$^2$. Generally desirable to use much more than the minimum amounts specified since the object of this tape is to apply enough debriding enzyme so that the burn or ulcer is debrided of necrotic tissue within 24 hours. However, if the amount of debriding enzyme applied is too great, then it is possible that the debridement will occur too deeply and that there will be blood loss because the vessel walls will be lysed by the enzyme. To avoid this, a single dose can be applied on the debriding tape, as frequently as is necessary for complete debridement. To illustrate with the most preferred debriding enzymes, this single dose would be about 2000 PCU/cm$^2$ of subtilisin per square centimeter of eschar to be removed. Thus, while the amounts are not truly critical in terms of what is operative, it is possible to have too little or too much, and in general, we have found that operative limits using subtilisin are 1000 to 4000 PCU per square centimeter of eschar to be removed. With other enzymes, the specific amounts are different. It is possible to equate many of the various proteolytic enzymes which may be used by referring to units of casein hydrolysis activity (PCU), so if the same units are used, then the different amounts necessary of the specific debriding enzyme which is chosen can be equated. On the other hand, some enzymes, such as the escharase fraction of bromelain, may require definition of their activity in other types of units.

Tape Backings and Adhesives

The backings which are useful for purposes of the present invention are those commonly used for medical, surgical or tape purposes which are either fully occlusive or semi-occlusive, i.e., having a moisture-vapor transmission rate ranging from about 200 grams per 100 square inches per 24 hours penetration down to zero.

A highly evaporative dressing cannot be used in the debriding tape of the present invention since it allows moisture to evaporate through the dressing which results in drying and inactivation of the debriding enzyme so that it is no longer effective. The reason for not being able to use a highly evaporative dressing is that it is necessary for water from (or placed on) the wound being treated to be held in place under the dressing so that it puddles and serves to activate the enzyme and is not transmitted through the dressing, wicking the enzyme away from the necrotic tissue. The debriding enzymes of the present invention are not effective in their dry state, but only are activated when they are exposed to water. Wounds of the nature of the burns or ulcers which the debriding tapes of the present invention will be used for do permit enough water loss for enzyme activation. However, the debriding action of the tape can be hastened by application of water to the eschar or necrotic tissue just before applying the debriding tape.

The specific material that the occlusive or semi-occlusive dressing is made from is not critical. We have found a polyurethane backing to be excellent but any backing which is useful for medical or surgical dressing purposes should be satisfactory. The polyurethane backing used in the tape of our examples is transparent. This is a desirable, but not a critical attribute for our tape backings. The advantage of a transparent backing is to permit inspection of the eschar being debrided.

The particular adhesive used in the tape of the specific example is a pressure-sensitive acrylate type, but the specific nature of the adhesive mass is not truly critical as long as it is acceptable for medical or surgical purposes, it does not react with or inactivate the debriding enzyme, and is capable of holding the debriding enzyme powder particles in place. Naturally, adhesives which do not adversely affect the skin are preferred. Of course, patients with burns and ulcers are in a sensitive condition so it is desired that the adhesive which will surround the very tender areas be easy to remove and not cause any undue pain or skin damage.

The debriding tapes of the present invention are to be used to debride second or third degree burns and grade two to grade four ischemic ulcers, or any wound containing necrotic tissue.

The size of the active portion of the debriding tape, i.e., the portion containing the debriding enzyme on it should be such as to cover the burn or other necrotic tissue site completely plus a small amount of the surrounding intact skin. Thus, tapes of varying sizes are contemplated.

Each debriding tape may have an optional border of adhesive without enzyme for adhesive purposes.

The use of the debriding tape of the present invention serves to perform two major additional debriding therapy functions which would otherwise need to be done separately. First, life-threatening water loss through the burned skin is reduced by topical occlusion preserving patient homeostasis. Second, the tape acts as a bacterial barrier, preventing exogenous bacteria from reaching and infecting the burned tissue.

OTHER ADVANTAGES OF THE INVENTION

The preferred debriding tape of the present invention is clear when moist, allowing a view of the wound for diagnostic purposes without painful removal of the dressing. This contrasts sharply with existing products which must be dressed with layers of wet gauze.

Debriding enzymes are very painful in actual operation. Thus, it is desirable to use the least amount possible which is still effective. The application of a debriding tape is effective in reducing pain, since a lesser amount of enzyme is actually used than is in the commercially available debriding ointments.

Furthermore, the inadvertent application of any part of the active portion of the debriding tape to healthy skin will not be painful, as contrasted to applying a debriding ointment, because while the debriding enzyme in the moist ointment is activated, the debriding enzyme on the debriding tape is not activated except in the presence of water, and covering normal skin with the debriding tape will not result in water accumulating above the normal skin nearly as quickly as it does over a burn or wound.

The debriding tapes sustain a moist environment for 24 hours, if necessary, allowing the enzymes to act continuously without the repeated dressing changes 3 to 4 times daily required by existing enzyme products.

The debriding tapes can be sterilized in a manner which will not activate the debriding enzymes prematurely, e.g., by irradiation. The debriding tapes of the present invention can be sterilized in sealed packages and be available for actual use, whenever desired, still in sterile form. Moreover, each debriding tape will be sterile when opened and applied. The few existing formulations which are sterile only are so upon first use.

The debriding tapes of the present invention are stable at room temperature (or temperatures below 40° C.) and need not be refrigerated, when packaged in a sealed waterproof container of the type surgical, pressure-sensitive adhesive tapes are normally packaged in to maintain their sterility. In aging tests, debriding tapes have lasted as long as 150 days and still maintained potent activity, so they should be stable for much longer time periods. This is a great advantage for use under battle conditions, emergency conditions, and even in hospitals.

Incorporating silver sulfadiazine on or in the adhesive mass of the debriding tape could be quite desirable since it will offer slow release of the silver sulfadiazine which will act as an antibacterial agent while the debriding is occurring. This is especially important because necrotic tissue is an excellent growing medium for bacteria. Tests were conducted in which silver sulfadiazine, which is a powder, was mixed in with the adhesive mass of a tape. The debriding enzyme was then applied to the adhesive surface of the tape. It was found that the silver sulfadiazine did not adversely affect the debriding abilities of the activated enzyme. Tapes with silver sulfadiazine may be sterilized also as described above.

EXAMPLE

The various debriding tapes of the present invention referred to here were made by the following laboratory-type general procedure.

In the tests referred to herein, the debriding tape utilized was made from a commercially-available BIOCLUSIVE* Transparent Dressing (Johnson & Johnson Products, Inc.). This dressing is similar to that described in U.S. Pat. No. 4,413,621, which is a very thin (1.5 mil or 0.0375 mm thick) polyether polyurethane film having a moisture vapor transmission rate of at least 15 grams per 100 square inches per 24 hours but which is impervious to liquid water and to bacteria coated with an acrylate-type surgical pressure-sensitive adhesive having a release sheet covering the adhesive coating.

Utilizing a BIOCLUSIVE Transparent Dressing, the dressing is partially pulled back from the silicone-coated release paper and a hole is cut into the release paper of the desired size, for example, a 22 millimeter diameter circle, and the dressing is thereupon put back onto the release paper so that the cut-out circle has no release paper on it, but the adhesive side of the dressing is exposed. Five thousand PCU of subtilisin A (or the desired amount of the desired debriding agent) powder are applied to the cut-out 6 $cm^2$ portion, and a straight edge is used to distribute the subtilisin (or other) powder evenly over the cut-out area by a reciprocating motion with the straight edge. Then a protective facing of release paper is applied so that the subtilisin (or other) powder on the adhesive is completely covered until the resultant debriding tape is ready for use. In carrying out the specific tests shown in Table 1, the debriding tape so made was not sterilized.

However, for commercial use, it is contemplated that the debriding tape likely will be sterilized, for example, by the use of cobalt irradiation at 2.5 megarads, and in other tests such a method of sterilization has been shown not to adversely affect the debriding properties of the debriding tape so made.

While the above procedure has been used in our laboratory tests, the debriding tape of the present invention can be made differently, as it undoubtedly will be for large-scale commercial purposes, and it is not contemplated that it will be necessary to utilize cut-out release paper in actual commercial use. Instead, the desired quantity of the debriding enzyme could be deposited directly using electrostatic spray, electrostatic flocculation, electrostatic deposition, air spray, spray or ink jet or any satisfactory techniques on the adhesive mass side of the occlusive tape backing and release paper will thereupon be placed over the entire adhesive side of the tape backing including those portions covered with the debriding enzyme.

Test Procedure

Burn eschar is relatively hard and cannot be easily removed. Debriding enzymes serve to soften the eschar so it is easily removable, for example, with a moistened gauze sponge. The force necessary to penetrate the eschar with a blunt surface is a good measure of the effectiveness of any debridement which has occurred. The following quantitative test for debridement was developed and utilized in connection with the present invention. In interpreting the results obtained, smaller numbers indicate better debriding activity, and larger numbers indicate a lesser debriding activity has occurred.

Method

Circular full-thickness burn wounds 4 square cm in area were made bilaterally on the dorsal flanks of guinea pigs. Six wounds were used for each experimental condition studied. Each wound was made by applying water at 90° C. for 15 seconds to the skin which had been ZIP-WAX ® depilated at least 4 days before burning.

A measured amount of the enzyme preparation to be evaluated was then applied immediately to the burn site or to the adhesive mass of BIOCLUSIVE transparent dressing, which covered all wounds and was held in place for 24 hours with elastic tape. The amount of enzyme preparation applied to the wound was determined as that which covered the burn uniformly with a layer of material without falling or dripping off. For liquids, this was 0.25 ml; for creams or ointments, 1 ml; and for solids, 2 to 10 mg. All creams, ointments or lotions were covered with eight plies of gauze sponge to prevent migration of the treatment from the burn site.

Specific amounts of each material applied to the burns are listed in Tables 1 and 2.

At 2 or 24 hour intervals after application, the dressings were removed. Each wound was photographed and observed for irritation and bleeding. Then the density of the necrotic tissue was measured as the force required to penetrate the eschar with the blunt end of a Chatillon Spring Gauge (John Chatillon & Sons, Kew Gardens, New York). These measurements correlate well with the softness of the eschar, with readings of less than 100 g corresponding to eschars which are easily removable using a moistened gauze sponge, and readings of less than 300 g removable using a blunt spatula. They also match histological observations of necrotic tissue disintegration.

the debriding tape. Table 2A illustrates the effectiveness of several proteolytic enzymes, delivered from the adhesive surface of an occlusive tape, as described in the present invention. Table 2B demonstrates that carrier tapes with lower moisture vapor transmission (MVT) rates husband body fluids at the enzyme-tissue interface, increasing debriding activity. Additional experiments showed that premoistening the burn site by applying a moist sponge before application of the debriding tape reduced eschar density to 200 g after only two hours of treatment. Similar premoistening of a TRAVASE-treated burn did not produce this effect, possibly because much of the enzyme is trapped in the ointment vehicle and incapable of immediate activation.

TABLE 1

Effectiveness of commercially available enzyme products in softening burn eschars after 24 hours of treatment.

| Product (quantity applied) | Mean eschar density ± s.e.m. (grams of force to penetrate the burn eschar) | Number of Observation |
| --- | --- | --- |
| SANTYL Ointment (1 ml = 250 units of collagenase activity) | 460 ± 36 | 6 |
| ELASE Ointment (1 ml = 1 unit of fibrinolysin activity + 667 units, desoxyribonuclease) | 480 ± 18 | 6 |
| TRAVASE Ointment (1 ml = 82,000 proteolytic casein units) | 106 ± 20* | 12 |
| Untreated Control Burns | 500 ± 0 | 18 |

*significant debriding activity.

TABLE 2

Effectiveness of debriding agents on adhesive mass in softening burn eschars after 24 hours of treatment.

A. Under occlusive tapes:

| Enzyme | Units of Activity Applied | Mean eschar density ± s.e.m. (g force to penetrate eschar) | Number of Observations |
| --- | --- | --- | --- |
| Bromelain | 2100 PCU | 66 ± 40* | 6 |
|  | 525 PCU | 80 ± 43* | 6 |
| α Chymotrypsin | 1219 USPU | 100 ± 82* | 6 |
| Collagenase | 10 U | 300 ± 85 | 6 |
| Deoxyribonuclease | 3120 U | 416 ± 38 | 6 |
| Elastase | 20 U | 500 ± 0 | 6 |
| Pancreatic Lipase II | 832 U | 91 ± 45* | 6 |
| Subtilisin A | 2500 PCU | 7 ± 1* | 12 |
| Trypsin (lyophilized) | 1500 U | 75 ± 48* | 6 |

B. Bromelain (2100 PCU) on adhesive mass of commercial tapes with varying moisture vapor transmission (MVT) rates.

| Tape | MVT (g/100 in$^2$/24 hr) | Mean eschar density ± s.e.m. (g force to penetrate eschar) | Number of Observations |
| --- | --- | --- | --- |
| BIOCLUSIVE | 31 | 0 ± 0* | 6 |
| DERMILITE Paper Tape | 170 | 200 ± 72* | 6 |
| ELASTIKON | 440 | 500 ± 0 | 6 |
| Perforated BIOCLUSIVE | >500 | 500 ± 0 | 6 |

*significant debriding activity.

Results

The results are reported in Tables 1 and 2. The most effective debriding agents in this wound model were bromelain, chymotrypsin, pancreatic lipase, subtilisin A, and trypsin.

The only commercially available product (Table 1) which showed significant debriding activity was TRAVASE Ointment, which contains nearly 40 times the proteolytic activity present in the equally effective debriding tape of the present invention.

The results in Table 2 underscore the role of occlusion in sequestering fluids which activate the enzyme on

What is claimed is:

1. A debriding tape comprising a surgical adhesive tape comprising an adhesive mass on a non-gel, non-bioerodable, biocompatible, occlusive or semi-occlusive backing, said surgical adhesive tape having a lower moisture vapor transmission rate below 200 grams per 100 square inches per 24 hours, containing on the adhesive mass surface to be applied to a burn or other wound requiring debridement, an effective amount of a debriding enzyme useful for debridement of eschar and necrotic tissue, said debriding enzyme being in dry powdered form.

2. The debriding tape of claim 1 wherein the debriding enzyme is bromelein or any active fraction of bromelain or subtilisin A or sublitisin B.

3. The debriding tape of claim 1 wherein the adhesive tape is made from a polyurethane backing.

4. The debriding tape of claim 1 which has been sterilized.

5. The debriding tape of claim 1 which also contains an anti-bacterially effective amount of silver sulfadiazine on or in the same adhesive mass.

6. The debriding tape of claim 1 in which the surgical adhesive tape backing is made from polyurethane which is 1.5 mils thick, the adhesive mass is made from amine containing acrylate polymers, and the debriding enzyme is subtilisin A or B.

7. The debriding tape of claim 1 in which the surgical adhesive tape is made from a transparent polyurethane.

8. A sealed package containing the debriding tape of claim 1 which has been sterilized.

9. The package of claim 8 in which the debriding tape is stable when stored at temperatures below 40° C.

* * * * *

UNITED STATES PATENT AND TRADEMARK OFFICE
CERTIFICATE OF CORRECTION

PATENT NO. : 4,668,228

DATED : May 26, 1987

INVENTOR(S) : Laura Lee Bolton et al.

It is certified that error appears in the above-identified patent and that said Letters Patent is hereby corrected as shown below:

Column 9, line 6: after "tape" insert --backing--

Column 10, line 7: after "tape" insert --backing--

Signed and Sealed this

Twenty-second Day of December, 1987

Attest:

DONALD J. QUIGG

Attesting Officer

Commissioner of Patents and Trademarks